(12) United States Patent
Makino

(10) Patent No.: US 6,414,005 B1
(45) Date of Patent: Jul. 2, 2002

(54) HETEROCYCLIC COMPOUNDS HAVING NOS INHIBITORY ACTIVITIES

(75) Inventor: Toshihiko Makino, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/530,752

(22) PCT Filed: Nov. 4, 1998

(86) PCT No.: PCT/JP98/04967

§ 371 (c)(1),
(2), (4) Date: May 4, 2000

(87) PCT Pub. No.: WO99/23069

PCT Pub. Date: May 14, 1999

(30) Foreign Application Priority Data

Nov. 4, 1997 (JP) .............................................. 9-339267
Apr. 20, 1998 (JP) ........................................... 10-146492

(51) Int. Cl.⁷ .................... A61K 31/40; A61K 31/4155; C07D 231/12
(52) U.S. Cl. ..................... 514/383; 514/406; 514/427; 548/375.1; 548/265.8; 548/563
(58) Field of Search .................................. 514/406, 427, 514/383; 548/375.1, 563, 265.8

(56) References Cited

U.S. PATENT DOCUMENTS

| 4,386,099 A | | 5/1983 | Cereda et al. |
| 4,465,841 A | | 8/1984 | Cereda et al. |
| 5,223,526 A | * | 6/1993 | McLoughlin et al. ....... 514/406 |
| 5,629,335 A | * | 5/1997 | Manning et al. ............ 514/407 |
| 5,639,770 A | | 6/1997 | Chihiro et al. |
| 5,668,159 A | | 9/1997 | Jin et al. |

FOREIGN PATENT DOCUMENTS

| WO | WO 95/05363 | 2/1995 |
| WO | WO 96/19440 | 6/1996 |
| WO | 97 36860 | 10/1997 |
| WO | WO 97/46515 | 12/1997 |

OTHER PUBLICATIONS

Ferroni et al., "Guanidinophenyl Derivative of Pyrazole: Synthesis and Inhibitory Effect on Serine Proteinases, Blood Coagulation and Platelet Aggregation", *Ed. Sci.*, vol. 41, No. 10, pp. 747–757, (1986).

* cited by examiner

Primary Examiner—Joseph K. McKane
Assistant Examiner—Sonya Wright
(74) Attorney, Agent, or Firm—Browdy and Neimark

(57) ABSTRACT

Compounds represented by the general formula (1):

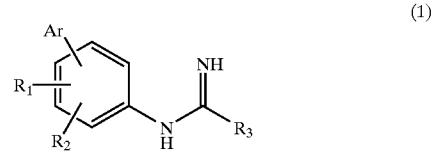

[wherein $R_1$ is typically an aminoalkyl group; $R_2$ is typically a hydrogen atom, a lower alkyl group, $R_3$ or $SR_4$ (where $R_4$ is typically a lower alkyl group); Ar is typically a 5-membered aromatic heterocyclic group] have an NOS inhibiting activity and are useful as therapeutics of cerebrovascular diseases and other pharmaceuticals.

28 Claims, No Drawings

HETEROCYCLIC COMPOUNDS HAVING NOS INHIBITORY ACTIVITIES

CROSS REFERENCE TO RELATION APPLICATIONS

The present application is the national stage under 35 U.S.C. 371 of PCT/JP98/04967, filed Nov. 4, 1998.

TECHNICAL FIELD

This invention relates to heterocyclic compounds, more particularly to compounds represented by the general formula (I) that have a nitric oxide synthase (NOS) inhibiting action to suppress the production of nitric oxide (NO) and thereby prove effective against disorders and diseases in which excessive NO or NO metabolites are supposedly involved, namely, cerebrovascular diseases [cerebral hemorrhage, subarachnoid hemorrhage, cerebral infarction (atherothromobotic infarction, lacunar infarction and cardiogenic embolism), transient ischemic attack and cerebral edema], traumatic brain injury, spinal injury, pains [headache (migraine, tension headache, cluster headache and chronic paroxysmal headache)], Parkinson's disease, Alzheimer's disease, seizure, and morphine tolerance or dependence. The invention also relates to possible tautomers, stereoisomers and optically active forms of said compounds, as well as pharmaceutically acceptable salts thereof. The invention further relates to preventives and therapeutics that contain said compounds or pharmaceutically acceptable salts as active ingredients.

BACKGROUND ART

The number of deaths from cerebrovascular diseases in Japan had increased until 1970 when it began to decline mostly due to the improvement in their acute-phase therapy. Nevertheless, cerebrovascular diseases remain the second leading cause of death among adult diseases, next only to cancers. As for the incidence of cerebrovascular diseases, many statistical surveys indicate that it is generally constant and in view of the fact that the number of elderly persons will increase at an uncomparably faster speed in Japan than any other country in the world, the number of patients suffering from cerebrovascular diseases is estimated to increase rather than decrease in the future. The declining mortality and the growing population of aged people combine to increase the cases of cerebrovascular diseases in the chronic phase and this has presented with a national problem not only from the aspects of individual patients and society at large but also from the viewpoint of medical economics since patients with chronic cerebrovascular disease are inevitably involved in long-term care. In cerebral infarction that accounts for most cases of cerebrovascular diseases, cerebral arteries are occluded and blood deficit starting at the blocked site extends to the peripheral site, causing an ischemic state. The symptoms of cerebral infarction in the chronic phase are in almost all cases derived from the loss of neurons and it would be extremely difficult to develop medications or established therapeutic methods for achieving complete recovery from those symptoms. Therefore, it is no exaggeration that the improvement in the performance of treatments for cerebral infarction depends on how patients in an acute phase can be treated with a specific view to protecting neurons and how far their symptoms can be ameliorated in the acute phase. However, most of the medications currently in clinical use are antiplatelet drugs, anticoagulants and thrombolytics and none of these have a direct nerve protecting action (see Kazuo MINEMATSU et al., "MEDICINA", published by Igaku Shoin, 32, 1995 and Hidehiro MIZUSAWA et al., published by Nankodo, "Naika" 79, 1997). Therefore, it is desired to develop a drug that provides an effective therapy for cerebrovascular diseases, in particular cerebral infarction, by working in an entirely novel and different mechanism of action from the conventional medications.

A presently dominant theory based on genetic DNA analyses holds that NOS exists in at least three isoforms, namely, calcium-dependent nNOS (type 1) which is present constitutively in neurons, calcium-dependent eNOS (type 3) which is present constitutively in vascular endothelial cells, and apparently calcium-independent iNOS (type 2) which is induced and synthesized by stimulation with cytokines and/or lipopolysaccharides (LPS) in macrophages and many other cells (Nathan et al., FASEB J. 16, 3051–3064, 1992; Nagafuji et al., Mol. Chem. Neuropathol. 26, 107–157, 1995).

A mechanism that has been proposed as being most probable for explaining the brain tissue damage which accompanies cerebral ischemia is a pathway comprising the sequence of elevation in the extracellular glutamic acid level, hyperactivation of glutamic acid receptors on the post-synapses, elevation in the intracellular calcium level and activation of calcium-dependent enzymes (Siesjö, J. Cereb. Blood Flow Metab. 1, 155–185, 1981; Siesjö, J. Neurosurg. 60, 883–908, 1984; Choi, Trends Neurosci. 11, 465–469, 1988; Siesjö and Bengstsson, J. Cereb. Blood Flow Metab. 9, 127–140, 1989). As already mentioned, nNOS is calcium-dependent, so the inhibition of hyperactivation of this type of NOS isoforms would contribute to the neuro-protective effects of NOS inhibitors (Dawson et al., Annals Neurol. 32, 297–311, 1992). As a matter of fact, the mRNA level of nNOS and the number of nNOS containing neurons start to increase early after focal cerebral ischemia in rats and their temporal alterations coincide with the development of infarction (Zhang et al., Brain Res. 654, 85–95, 1994). In an experiment with a mouse model of focal cerebral ischemia using $N^G$-nitro-L-arginine (L-NA) which is a NOS inhibitor, the percent inhibition of nNOS activity and the percent reduction of infarct volume correlated to each other at least in a dose range that produced a recognizable infarct volume reductive action (Carreau et al., Eur. J. Pharmacol. 256, 241–249, 1994). Further in addition, it has been reported that in nNOS knockout mice, the infarct volume observed after focal cerebral ischemia is significantly smaller than that in the control (Huang et al., Science 265, 1883–1885, 1994).

Referring now to NO, it is at least one of the essences of endothelium-derived relaxing factor (EDRF) and, hence, is believed to take part in the adjustment of the tension of blood vessels and the blood flow (Moncada et al., Pharmacol. Rev. 43, 109–142, 1991). As a matter of fact, it was reported that when rats were administered high doses of L-NA, the cerebral blood flow was found to decrease in a dose-dependent manner as the blood pressure increased (Toru MATSUI et al., Jikken Igaku, 11, 55–60, 1993). The brain has a mechanism by which the cerebral blood flow is maintained at a constant level notwithstanding the variations of blood pressure over a specified range (which is commonly referred to as "autoregulation mechanism") ("NOSOTCHU JIKKEN HANDBOOK", complied by Keiji SANO, published by IPC, 247–249, 1990). The report of Matsui et al. suggests the failure of this "autoregulation mechanism" to operate. Therefore, if eNOS is particularly inhibited beyond a certain limit in an episode of brain ischemia, the cerebral blood vessel will contract and the cerebral blood flow will decrease, thereby aggravating the dynamics of microcirculation, possibly leading to an expansion of the ischemic lesion. It was also reported that in eNOS knockout mice, the infarct observed after focal cerebral ischemia was larger than that in the control but could be reduced significantly by administration of L-NA (Huang et al., J. Cereb. Blood Flow Metab. 16, 981–987, 1996). These reports show that eNOS-derived NO probably works protectively on the brain tissue through the intermediary of a vasodilating action, a platelet aggregation suppressing action and so forth.

The present inventors previously found that L-NA, already known to be a NOS inhibitor, possessed ameliorative effects on the brain edema and cerebral infarction following phenomena that developed after experimental cerebral ischemia (Nagafuji et al., Neurosci. Lett. 147, 159–162, 1992; Japanese Patent Public Disclosure No. 192080/1994), as well as necrotic neuronal cell death (Nagafuji et al., Eur. J. Pharmacol. Env. Tox. 248, 325–328, 1993). On the other hand, relatively high doses of NOS inhibitors have been reported to be entirely ineffective against ischemic brain damage and sometimes aggravating it (Idadecola et al., J. Cereb. Blood Flow Metab. 14, 175–192, 1994; Toshiaki NAGAFUJI and Toru MATSUI, Jikken Igaku, 13, 127–135, 1995; Nagafuji et al., Mol. Chem. Neuropathol. 26, 107–157, 1995). It should, however, be stressed that as a matter of fact, all papers that reported the changes of NO or NO-related metabolites in the brain and blood in permanent or temporary cerebral ischemic models agreed in their results to show the increase in the levels of those substances (Toshiaki NAGAFUJI and Toru MATSUI, Jikken Igaku, 13, 127–135, 1995; Nagafuji et al., Mol. Chem. Neuropathol. 26, 107–157, 1995).

One of the reasons for explaining the fact that conflicting reports have been made about the effectiveness of NOS inhibitors in cerebral ischemic models would be the low selectivity of the employed NOS inhibitors for nNOS. As a matter of fact, no existing NOS inhibitors including L-NA and $N^G$-nitro-L-arginine methyl ester (L-NAME) have a highly selective inhibitory effect on a specific NOS isoform (Nagafuji et al. Neuroreport 6, 1541–1545, 1995; Nagafuji et al. Mol. Chem. Neuropathol. 26, 107–157, 1995). Therefore, it may well be concluded that desirable therapeutics of ischemic cerebrovascular diseases should have a selective inhibitory effect on nNOS (Nowicki et al., Eur. J. Pharmacol. 204, 339–340, 1991; Dawson et al., Proc. Natl. Acad. Sci. USA 88, 6368–6371, 1991; Iadecola et al., J. Cereb. Blood Flow Metab. 15, 52–59, 1995; Iadecola et al., J. Cereb. Blood Flow Metab. 15, 378–384, 1995; Toshiaki NAGAFUJI and Toru MATSUI, Jikken Igaku 13, 127–135, 1995; Nagafuji et al., Mol. Chem. Neuropathol. 26, 107–157, 1995; Iadecola et al., Am. J. Physiol. R286-R292, 1995).

It has also been suggested that nNOS inhibitors have the potential for use as therapeutics of traumatic brain injuries (Oury et al., J. Biol. Chem. 268, 15394–15398, 1993; MacKenzie et al., Neuroreport 6, 1789–1794, 1995; Mesenge et al., J. Neurotrauma. 13, 11–16, 1996; Wallis et al., Brain Res., 710, 169–177, 1996), headache and other pains (Moore et al., Br. J. Pharmacol. 102, 198–202, 1991; Olesen., Trends Pharmacol. 15, 149–153, 1994), Parkinson's disease (Youdim et al., Advances Neurol. 60, 259–266, 1993; Schulz et al., J. Neurochem. 64, 936–939, 1995; Hantraye et al., Nature Medicine 2, 1017–1021, 1996), Alzheimer's disease (Hu and EI-FaKahany, Neuroreport 4, 760–762, 1993 Meda et al., Nature 374, 647–650, 1995), seizure (Rigaud-Monnet et al., J. Cereb. Blood Flow Metab.

14, 581–590, 1994), and morphine tolerance and dependence (Kolesnikov et al., Eur. J. Pharmacol. 221, 399–400, 1992; Cappendijk et al., Neurosci. Lett. 162, 97–100, 1993).

The NOS inhibitors so far reported to have a certain degree of selectivity for nNOS are $N^G$-cyclopropyl-L-arginine (L-CPA)(Lamberte et al., Eur. J. Pharmacol. 216, 131–134, 1992), L-NA (Furfine et al., Biochem. 32, 8512–8517, 1993), S-methyl-L-thiocitrulline (L-MIN) (Narayanan and Griffith, J. Med. Chem. 37, 885–887, 1994; Furfine et al., J. Biol. Chem. 37, 885–887, 1994; Furfine et al. J. Biol. Chem. 269, 26677–26683, 1994; WO95/09619; Narayanan et al., J. Biol. Chem. 270, 11103–11110, 1995; Nagafuji et al., Neuroreport 6, 1541–1545, 1995), S-ethyl-L-thiocitrulline (L-EIN) (Furfine et al., J. Biol. Chem. 269, 26677–26683, 1994; WO95/09619; Narayanan et al.,J. Biol. Chem. 270, 11103–11110, 1995), and ARL 17477 (Gentile et al., WO95/05363; Zhang et al., J. Cereb. Blood Flow Metab., 16, 599–604, 1996). WO96/18608 lists compounds showing nNOS inhibiting activity.

DISCLOSURE OF INVENTION

An object of the present invention is to provide novel compounds that have a selective inhibitory effect on calcium-dependent nNOS which is present constitutively in the brain, particularly in neurons, and which are useful as therapeutics of cerebrovascular diseases [cerebral hemorrhage, subarachnoid hemorrhage, cerebral infarction (atherothrombotic infarction, lacunar infarction and cardiogenic embolism), transient ischemic attack and cerebral edema], traumatic brain injury, spinal injury, pains [headache (migraine, tension headache, cluster headache and chronic paroxysmal headache)], Parkinson's disease, Alzheimer's disease, seizure, and morphine tolerance or dependence.

As a result of the intensive studies made in order to attain the stated object, the present inventors found that heterocyclic compounds represented by the general formula (1), or possible tautomers, stereoisomers and optically active forms of said compounds, as well as pharmaceutically acceptable salts thereof have an nNOS inhibitory action or selectivity greater than any existing NOS inhibitors, thereby exhibiting marked effectiveness as therapeutics of cerebrovascular diseases (especially as therapeutics of occlusive cerebrovascular diseases):

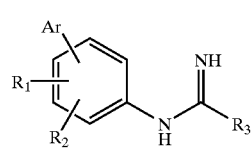

(1)

(wherein
$R_1$ is an optionally substituted aminoalkyl group having 1–6 carbon atoms in the alkyl moiety;
$R_2$ is a hydrogen atom, a lower alkyl group or a halogen atom;
$R_3$ is an optionally substituted lower alkyl group, $SR_4$, $OR_4$ or $NR_5R_6$ provided that $R_4$ is a lower alkyl group that may be substituted by a halogen atom and $R_5$ and $R_6$, which may be the same or different, represent a hydrogen atom, a lower alkyl group or a nitro group or, when taken together, may form a 3- to 6-membered ring; and
Ar is an optionally substituted 5- or 6-membered aromatic heterocyclic group).

The present invention has been accomplished on the basis of this finding.

The aminoalkyl group having 1–6 carbon atoms in the alkyl moiety means an aminoalkyl group having the alkyl moiety of which is a straight-chained alkyl having 1–6 carbon atoms or an aminoalkyl group having the alkyl moiety of which is a cyclic alkyl having 3–6 carbon atoms, and examples include an aminomethyl group, a 2-aminoethyl group, a 3-aminopropyl group, a 4-aminobutyl group, a 5-aminopentyl group, a 6-aminohexyl group, a 1-aminocyclopropyl group, a 2-aminocyclopropyl group, a 1-aminocyclobutyl group, a 2-aminocyclobutyl group, 3-aminocyclobutyl group, a 1-aminocyclopentyl group, a 2-aminocyclopentyl group, a 3-aminocyclopentyl group, a 1-aminocyclhexyl group, a 2-aminocyclohexyl group, a 3-aminocyclohexyl group, a 4-aminocyclohexyl group, etc.

The lower alkyl group means a straight-chained alkyl group having 1–6 carbon atoms or a branched or cyclic alkyl group having 3–8 carbon atoms, and examples include a methyl group, an ethyl group, an n-propyl group, an n-butyl group, an n-pentyl group, an n-hexyl group, an i-propyl group, an i-butyl group, a sec-butyl group, a tert-butyl group, an i-pentyl group, a neopentyl group, a tert-pentyl group, an i-hexyl group, a cyclopropyl group, a cyclobutyl group, a cyclopentyl group, a cyclohexyl group, a cycloheptyl group, a cyclooctyl group, etc.

The halogen atom is a fluorine atom, a chlorine atom, a bromine atom or an iodine atom.

The 5- or 6-membered aromatic heterocyclic group contains at least one nitrogen atom and may optionally contain an oxygen atom or a sulfur atom and examples include a pyrrol-1-yl group, a pyrrol-2-yl group, a pyrrol-3-yl group, a pyrazol-1-yl group, a pyrazol-3-yl group, a pyrazol-4-yl group, an imidazol-1-yl group, an imidazol-2-yl group, an imidazol-4-yl group, a 1,2,3-triazol-1-yl group, a 1,2,4-triazol-1-yl group, a 1,2,4-triazol-3-yl group, a 1H-tetrazol-1-yl group, an isoxazol-3-yl group, an isoxazol-4-yl group, an isoxazol-5-yl group, an isothiazol-3-yl group, an isothiazol-4-yl group, an isothiazol-5-yl group, an oxazol-2-yl group, an oxazol-4-yl group, an oxazol-5-yl group, a thiazol-2-yl group, a thiazol-4-yl group, a thiazol-5-yl group, a pyridin-2-yl group, a pyridin-3-yl group, a pyridin-4-yl group, a pyridazin-3-yl group, a pyridazin-4-yl group, a pyrimidin-2-yl group, a pyrimidin-4-yl group, a pyrimidin-5-yl group, a pyrazin-2-yl group, a 1,2,4-triazin-3-yl group, a 1,2,4-triazin-5-yl group, a 1,2,4-triazin-6-yl group, a 1,3,5-triazin-2-yl group, etc.

The substituent in $R_1$ and Ar may be exemplified by a lower alkyl group, a phenyl group, a benzyl group and a phenethyl group.

The substituent in $R_3$ may be exemplified by a halogen atom, a lower alkoxy group and a lower alkylthio group.

The lower alkoxy group means a straight-chained alkoxy group having 1–6 carbon atoms or a branched or cyclic alkoxy group having 3–8 carbon atoms, and examples include a methoxy group, an ethoxy group, an n-propoxy group, an n-butoxy group, an n-pentoxy group, an n-hexoxy group, an i-propoxy group, an i-butoxy group, a sec-butoxy group, a tert-butoxy group, an i-pentoxy group, a neopentoxy group, a tert-pentoxy group, an i-hexoxy group, a cyclopropoxy group, a cyclobutoxy group, a cyclopentoxy group, a cyclohexoxy group, a cycloheptoxy group, a cyclooctoxy group, etc.

The lower alkylthio group is a straight-chained alkylthio group having 1–6 carbon atoms or a branched or cyclic alkylthio group having 3–8 carbon atoms, and examples include a methylthio group, an ethylthio group, an n-propylthio group, an n-butylthio group, an n-pentylthio group, an n-hexylthio group, an i-propylthio group, an i-butylthio group, a sec-butylthio group, a tert-butylthio group, an i-pentylthio group, a neopentylthio group, a tert-pentylthio group, an i-hexylthio group, a cyclopropylthio group, a cyclobutylthio group, a cyclopentylthio group, a cyclohexylthio group, a cycloheptylthio group, a cyclooctylthio group, etc.

The optionally substituted lower alkyl group as $R_3$ is preferably a lower alkyl group having 1–4 carbon atoms that may be substituted by a halogen atom, a lower alkoxy group or a lower alkylthio group, and examples include a methyl group, a fluoromethyl group, a methoxymethyl group, an ethoxymethyl group, a methylthiomethyl group, an ethylthiomethyl group, an ethyl group, a 2-fluoroethyl group, a 2,2,2-trifluoroethyl group, a 2-chloroethyl group, a 2-methoxyethyl group, a 2-methylaminoethyl group, an n-propyl group, an i-propyl group, a 1-methylthiopropyl group, an n-butyl group, an i-butyl group, etc.

A preferred example of $SR_4$ as $R_3$ is a lower alkylthio group having 1–3 carbon atoms that may be substituted by a halogen atom, as exemplified by a methylthio group, an ethylthio group, a 2-fluoroethylthio group, a 2,2,2-trifluoroethylthio group, a 2-chloroethylthio group, an n-propylthio group, an i-propylthio group, etc.; an ethylthio group is particularly preferred.

A preferred example of $OR_4$ as $R_3$ is a lower alkoxy group having 1–3 carbon atoms that may be substituted by a halogen atom, as exemplified by a methoxy group, an ethoxy group, a 2-fluoroethoxy group, a 2,2,2-trifluoroethoxy group, a 2-chloroethoxy group, an n-propoxy group, an i-propoxy group, etc.

The lower alkyl group as $R_5$ and $R_6$ is preferably a lower alkyl having 1–3 carbon atoms.

The cyclic group that may form a 3- to 6-membered ring of $R_5$ and $R_6$ when combined together is preferably a 5- or 6-membered heterocyclic group containing at least one nitrogen atom.

A preferred example of $NR_5R_6$ as $R_3$ is a primary or secondary amino group that may be substituted by a lower alkyl group of 1–3 carbon atoms or a nitro group or a 5- or 6-membered heterocyclic group containing at least one nitrogen atom, as exemplified by an amino group, a methylamino group, an ethylamino group, an n-propylamino group, an i-propylamino group, a dimethylamino group, an ethylmethylamino group, a nitroamino group, a pyrrolidin-1-yl group, a piperidino group, a morpholino group, a pyrrol-1-yl group, a pyrrol-2-yl group, a pyrrol-3-yl group, a pyrazol-1-yl group, a pyrazol-3-yl group, a pyrazol-4-yl group, an imidazol-1-yl group, an imidazol-2-yl group, an imidazol-4-yl group, a 1,2,3-triazol-1-yl group, a 1,2,4-triazol-1-yl group, a 1,2,4-triazol-3-yl group, a 1H-tetrazol-1-yl group, a pyridin-2-yl group, a pyridin-3-yl group, a pyridin-4-yl group, a pyridazin-3-yl group, a pyridazin-4-yl group, a pyrimidin-2-yl group, a pyrimidin-4-yl group, a pyrimidin-5-yl group, a pyrazin-2-yl group, a 1,2,4-triazin-3-yl group, a 1,2,4-triazin-5-yl group, a 1,2,4-triazin-6-yl group, a 1,3,5-triazin-2-yl group, etc.

A preferred example of $R_1$ is an aminoalkyl group the alkyl moiety of which is a straight-chained alkyl having 1–3 carbon atoms and an aminomethyl group is particularly preferred.

A preferred example of $R_2$ is a hydrogen atom or a lower alkyl group and a hydrogen atom or a methyl group is particularly preferred.

A preferred example of $R_3$ is $SR_4$, with a lower alkylthio group being more preferred and an ethylthio group being particularly preferred.

A preferred example of Ar is a 5-membered aromatic heterocyclic group; a more preferred example is an aromatic heterocyclic group containing a nitrogen atom, and a pyrrol-1-yl group and a pyrazol-1-yl group being particularly preferred.

Except for $R_2$ and Ar, the benzene nucleus is preferably m-substituted.

The preferred examples of the compound represented by the general formula (1) include N-(3-aminomethyl-4-(pyrazol-1-yl)phenyl)-S-ethylisothiourea, N-(3-aminomethyl-4-(pyrrol-1-yl)phenyl)-S-ethylisothiourea and N-(3-aminomethyl-2-methyl-4-(pyrazol-1-yl)phenyl)-S-ethylisothiourea.

BEST MODE FOR CARRYING OUT THE INVENTION

The compounds of the present invention which are represented by the general formula (1) can be synthesized by different methods depending on the specific type of $R_3$ and exemplary methods are as follows.

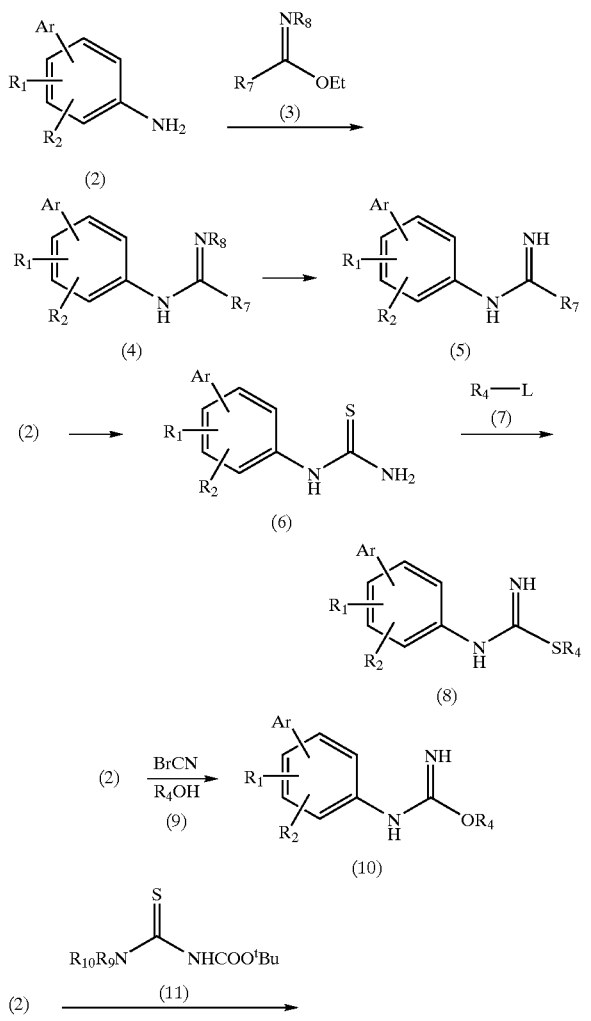

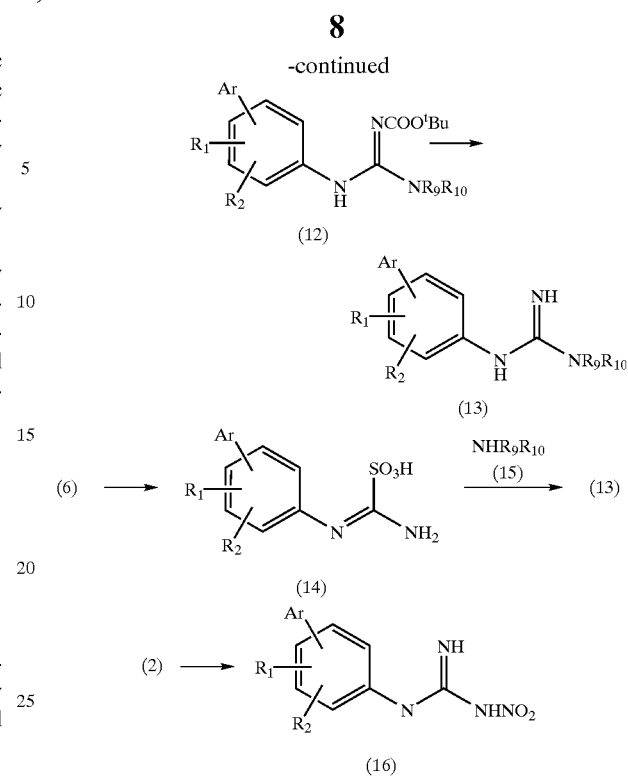

In the above formulas (2)–(16), $R_1$ is an optionally substituted aminoalkyl group the alkyl moiety of which has 1–6 carbon atoms, $R_2$ is a hydrogen atom, a lower alkyl group or a halogen atom, $R_4$ is a lower alkyl group that may be substituted by a halogen atom, $R_7$ is an optionally substituted lower alkyl group, $R_8$ is a tert-butoxycarbonyl group or a benzyloxycarbonyl group, $R_9$ and $R_{10}$ which may be the same or different represent a hydrogen atom or a lower alkyl group or, when taken together, may form a 3- to 6-membered ring, Ar is an optionally substituted 5- or 6-membered aromatic heterocyclic group, and L is a leaving group such as a chlorine atom, a bromine atom, an iodine atom, a trifluoromethanesulfonyloxy group, a p-toluenesulfonyloxy group or a methanesulfonyloxy group.

Among the compounds represented by the formula (1), a compound represented by the formula (5) wherein $R_3$ is $R_7$ can be synthesized by a process that starts with a compound represented by the formula (2) and which gives a compound represented by the formula (4) as an intermediate.

Specifically, a compound represented by the formula (2) and a compound represented by the formula (3) are reacted in the presence or absence of 4-dimethylaminopyridine in an inert solvent such as an alcohol (e.g. methanol, ethanol or i-propanol) or chloroform, methylene chloride, 1,2-dichloroethane, toluene or dimethylformamide, preferably in methylene chloride, at a temperature between 0° C. and the boiling point of the reaction mixture, preferably at room temperature, thereby giving a compound represented by the formula (4).

The resulting compound represented by the formula (4) has an amidino protecting group that is represented by $R_8$ and this protective group is removed under ordinary conditions to produce a compound represented by the formula (5).

The reaction for removing the amidino protecting group depends on the type of the protective group. If it is a tert-butoxycarbonyl group, the reaction is preferably performed either in an inert solvent such as methanol, ethanol or 1,4-dioxane or in a solvent-free condition at a temperature between 0° C. and room temperature using a deprotective agent such as trifluoroacetic acid, hydrochloric acid, sulfuric acid or methanesulfonic acid. It is particularly preferred to use trifluoroacetic acid at room temperature under anhydrous conditions.

If the amidino protecting group is a benzyloxycarbonyl group, it is removed by catalytic reduction reaction which can be performed with palladium-carbon or Raney's nickel or platinum oxide as a catalyst in an inert solvent such as ethanol, methanol, ethyl acetate, acetic acid or 1,4-dioxane, preferably in ethanol or methanol, under a hydrogen atmosphere at a temperature between room temperature and the boiling point of the reaction mixture, preferably at room temperature.

Among the compounds represented by the formula (1), a compound represented by the formula (8) wherein $R_3$ is $SR_4$ can be synthesized by a process that starts with a compound represented by the formula (2) and which gives a compound represented by the formula (6) as an intermediate.

Specifically, a compound represented by the formula (2) is reacted with benzoyl isothiocyanate in an inert solvent such as tetrahydrofuran, chloroform, methylene chloride or dimethylformamide at a temperature between −20° C. and the boiling point of the reaction mixture, preferably in acetone at room temperature. If necessary, the reaction mixture is concentrated after the end of the reaction and is further subjected to reaction in an inert solvent such as methanol in the presence of an inorganic base such as potassium carbonate or sodium hydroxide at a temperature between 0° C. and the boiling point of the reaction mixture, preferably in methanol in the presence of potassium carbonate at room temperature, thereby giving a compound represented by the formula (6).

The compound represented by the formula (6) can also be obtained by performing reaction on the compound of the formula (2) in accordance with the method of T. Makino et al. (WO96/18608).

Specifically, the compound represented by the formula (2) is first reacted with thiophosgene in the presence of an inorganic base such as calcium carbonate or potassium carbonate or an organic base such as triethylamine or 4-dimethylaminopyridine in an inert solvent such as chloroform, methylene chloride, water or dimethylformamide at a temperature between 0° C. and the boiling point of the reaction mixture, preferably in the presence of 4-dimethylaminopyridine in methylene chloride at room temperature and subsequently treated with conc. aqueous ammonia or saturated ammonia in methanol to give the compound of the formula (6).

The compound of the formula (6) can also be obtained by first reacting the compound of the formula (2) with benzoyl chloride or ammonium thiocyanate in an inert solvent such as acetone at a temperature between room temperature and the boiling point of the reaction mixture, preferably at room temperature, then heating the reaction mixture under reflux together with 10% sodium hydroxide solution.

In the next step, the compound of the formula (6) is reacted with a compound represented by the formula (7) in an inert solvent such as acetonitrile, acetone, 1,4-dioxane, methanol or ethanol at a temperature between room temperature and the boiling point of the reaction mixture, preferably in acetonitrile, as the reaction mixture is heated under reflux, thereby producing a compound represented by the formula (8).

Among the compounds represented by the formula (1), a compound represented by the formula (10) wherein $R_3$ is $OR_4$ can be synthesized by the following process starting with a compound represented by the formula (2).

The compound of the formula (2) is reacted with cyano bromide and a suitable type of alcohol represented by the formula (9) at a temperature between 0° C. and the boiling point of the reaction mixture, preferably at room temperature, to produce the compound represented by the formula (10).

Among the compounds represented by the formula (1), a compound represented by the formula (13) wherein $R_3$ is $NR_9R_{10}$ can be synthesized by a process that starts with a compound represented by the formula (2) and which gives a compound represented by either the formula (12) or (14) as an intermediate.

Specifically, the compound represented by the formula (2) is reacted with a compound represented by the formula (11) in accordance with the method of M. A. Poss (Tetrahedron Lett. 33, 5933–5936, 1992), thereby producing a compound of the formula (12), and the t-butoxycarbonyl protecting group is removed to yield a compound represented by the formula (13).

Alternatively, a compound represented by the formula (6) is converted to a compound represented by the formula (14) in accordance with the method of C. A. Maryanoff et al. (J. Org. Chem. 51, 1882–1884, 1986) and then reacted with an amine represented by the formula (15) so as to yield a compound represented by the formula (13).

Among the compounds represented by the formula (1), a compound represented by the formula (16) wherein $R_3$ is $NHNO_2$ can be synthesized by the following process starting with the compound of the formula (2).

The compound represented by the formula (2) is reacted with N-methyl-N'-nitro-N-nitrosoguanidine in an inert solvent such as acetonitrile, ethanol, methanol or water, preferably in acetonitrile, at a temperature between room temperature and the boiling point of the reaction mixture, preferably at room temperature, in the optional presence of added triethylamine or acetic acid, thereby producing the compound of the formula (16).

If, in the process of synthesizing the compounds represented by the above formulas (4), (5), (6), (8), (10), (12), (13), (14) and (16), there occurs a substituent that needs a protective group, a protecting reaction and a deprotecting reaction are performed in accordance with the type of the substituent. In principle, both reactions can be performed by the methods described in Greene and Wuts, "PROTECTIVE GROUPS IN ORGANIC SYNTHESIS", 2nd Edition, John Wiley & Sons Inc. For example, if the substituent that needs a protective group is a primary or secondary amino group, suitable protective groups include a tert-butoxycarbonyl group, a benzyloxycarbonyl group and a trifluoroacetyl group.

An amino group protecting reaction, for example, tert-butylcarbonylation, can be accomplished by reaction with di-tert-butyl dicarbonate in an inert solvent such as an alcohol (e.g. methanol, ethanol or i-propanol) or methylene chloride, dimethylformamide or 1,4-dioxane in the presence of an organic base such as triethylamine or 4-dimethylaminopyridine at a temperature between 0° C. and room temperature. Another amino group protecting reaction such as benzyloxycarbonylation can be accomplished by reaction with benzyl chlorocarbonate in an inert solvent such as methylene chloride in the presence of an organic base such as triethylamine or 4-dimethylaminopyridine at a temperature between 0° C. and room temperature. Yet another amino group protecting reaction such as trifluoroacetylation can be accomplished by reaction with trifluoroacetic anhydride in an inert solvent such as methylene chloride in the presence of an organic base such as triethylamine or pyridine at a temperature between 0° C. and room temperature.

Referring to the amino group deprotecting reaction, if the protective group is a tert-butoxycarbonyl group or a benzyloxycarbonyl group, the reaction can be performed under the same conditions as the reaction for removing the amidino protecting group. In the case of another protective group such as a trifluoroacetyl group, the deprotecting reaction can be accomplished either by reaction with potassium carbonate in methanol at room temperature or by reaction in 4 N HCl at 60° C.

If the compounds of the invention which are represented by the general formula (1) have asymmetric carbons in their structure, the pure forms of their stereoisomers and optically active forms can be obtained by known techniques in the art, such as chromatography on optical isomer separating columns and fractional crystallization.

Pharmaceutically acceptable salts of the compounds of the invention which are represented by the general formula (1) may be of any types as long as they are pharmaceutically acceptable salts and typical examples include salts with inorganic acids such as hydrochloric acid, sulfuric acid, nitric acid, hydrobromic acid and hydroiodic acid, salts with organic acids such as formic acid, acetic acid, fumaric acid and tartaric acid, salts with alkali metals such as sodium and potassium, and salts with alkaline earth metals such as calcium and magnesium.

The compounds of the invention or salts thereof may be formulated with suitable excipients, adjuvants, lubricants, antiseptics, disintegrators, buffering agents, binders, stabilizers, wetting agents, emulsifiers, coloring agents, flavoring agents, fragrances, etc. to form tablets, granules, subtilized granules, powders, capsules, syrups, elixirs, suspensions, emulsions, injections, etc. for oral or parenteral administration. When the cerebrovascular diseases to be treated are in a hyperacute phase (immediately after the stroke), an acute phase (from the stroke to 2 or 3 days later) or in a subacute phase (2 or 3 days up to 2 weeks after the stroke), it is anticipated that administration is effected primarily by intramuscular or intravenous injection. In addition, oral administration may be performed in a chronic phase (the third week after stroke and onward) if the patient admits ingestion.

The compounds of the invention or salts thereof may be administered in doses that vary with the physical constitution of the patient, his or her age, physical condition, the severity of the disease, the time of lapse after the onset of the disease and other factors; typical daily doses are anticipated to range from 0.1 to 100 mg/body. It should generally be noted that even if the same dose is administered, the plasma concentration may sometimes vary considerably between patients; hence, an optimal dose of the drug should ideally be determined for each patient on the basis of a monitored plasma concentration of the drug.

If the compounds of the invention or salts thereof are to be formulated as preparations for internal application, lactose, sucrose, sorbitol, mannitol, starches such as potato starch or corn starch, starch derivatives and common additives such as cellulose derivatives or gelatin are suitably used as vehicles, with lubricants such as magnesium stearate, carbowaxes and polyethylene glycol being optionally added concurrently; the resulting mixtures may be formulated in the usual manner into granules, tablets, capsules or other forms suitable for internal application.

If the compounds of the invention or salts thereof are to be formulated as aqueous preparations, effective amounts of the principal ingredients may be dissolved in distilled water for injection, with antioxidants, stabilizers, dissolution aids, buffering agents, preservatives, etc. added as required and, after complete solutions are formed, they are filtered, filled into ampules and sealed in the usual manner and sterilized by a suitable medium such as high-pressure vapor or dry heat so as to prepare injections.

If the compounds of the invention or salts thereof are to be formulated as lyophilized preparations, aqueous solutions having the principal ingredients dissolved in distilled water for injection may be freeze-dried in the usual manner; depending on the need, excipients that provide for easy lyophilization, such as sugars (e.g. lactose, maltose and sucrose), sugar alcohols (e.g. mannitol and inositol), glycine and the like, may be added before freeze-drying is performed in the usual manner to make the intended preparations.

The production of the compounds of the present invention is described below in greater detail with reference to working examples but it should be understood that the invention is by no means limited by those examples.

For the purpose of showing the utility of the present invention, tests were conducted to evaluate the effectiveness of selected compounds of the formula (1) in inhibiting various types of NOS.

EXAMPLES

A list of the compounds prepared in the Examples of the invention is given in Table 1 below.

TABLE 1

| Ex. No. | $R_1$ | $R_2$ | $R_3$ | Ar | Position of Ar | Salt |
|---|---|---|---|---|---|---|
| 1 | 3-$CH_2NH_2$ | H | SEt | pyrrole | 4 | 2HCl |

TABLE 1-continued

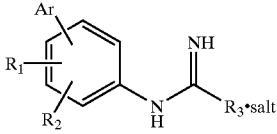

| Ex. No. | R₁ | R₂ | R₃ | Ar | Position of Ar | Salt |
|---|---|---|---|---|---|---|
| 2 | 3-CH$_2$NH$_2$ | H | SEt | 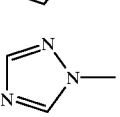 | 4 | 2HCl |
| 3 | 3-CH$_2$NH$_2$ | H | SEt | 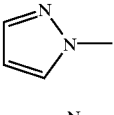 | 4 | 3HCl |
| 4 | 3-CH$_2$NH$_2$ | H | OEt | 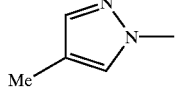 | 4 | 2HCl |
| 5 | 3-CH$_2$NH$_2$ | H | OEt | 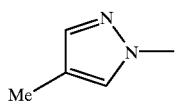 | 4 | 2HCl |
| 6 | 3-CH$_2$NH$_2$ | H | SEt | 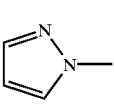 | 4 | 2HCl |
| 7 | 3-CH$_2$NH$_2$ | 2-Me | SEt | 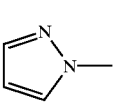 | 4 | 2HCl |
| 8 | 3-CH$_2$NH$_2$ | 2-Me | OEt |  | 4 | 2HCl |

Example 1

Synthesis of N-(3-aminomeththyl-4-(pyrrol-1-yl) phenyl)-S-ethylisothiourea dihydrochloride

Example 1a

Synthesis of 5-nitro-2-(pyrrol-1-yl)benzoic acid

A mixture of 2-amino-5-nitrobenzoic acid (475 mg), 2,5-dimethoxytetrahydrofuran (345 mg) and acetic acid (10 ml) was heated under reflux for 3 hours and then concentrated at reduced pressure. Brine was added to the resulting residue and the mixture was extracted with ethyl acetate. The organic layer was dried with anhydrous sodium sulfate and then concentrated at reduced pressure. The resulting residue was purified by silica gel column chromatography (eluent; ethyl acetate:n-hexane=1:1) to give the titled compound (yield, 73%).

$^1$H-NMR (CDCl$_3$) δ:6.38(2H,t,J=2.0 Hz), 6.88(2H,t,J=2.0 Hz), 7.55(1H,d,J=8.9 Hz), 8.43(1H,dd,J=2.6,8.9 Hz), 8.76 (1H,d,J=2.6 Hz)

Example 1b

Synthesis of 5-nitro-2-(pyrrol-1-yl)benzyl alcohol

To a solution in anhydrous tetrahydrofuran (10 ml) of the compound (392 mg) obtained in Example 1a, a borane-tetrahydrofuran complex (1.0 M, 2.2 ml) was added dropwise under a nitrogen atmosphere. After heating the reaction mixture under reflux for 3 hours, water was added and the mixture was concentrated at reduced pressure. Brine was added to the resulting residue and the mixture was extracted with ethyl acetate. The organic layer was dried with anhydrous sodium sulfate and concentrated at reduced pressure. The resulting residue was purified by silica gel column chromatography (eluent; ethyl acetate:dichloromethane= 1:19) to give the titled compound (yield, 70%).

$^1$H-NMR (CDCl$_3$) δ:1.99(1H,t,J=5.6 Hz), 4.72(2H,d,J= 5.6 Hz), 6.40(2H,t,J=2.0 Hz), 6.91(2H,t,J=2.0 Hz), 7.45(1H, d,J=8.6 Hz), 8.23(1H,dd,J=2.6,8.6 Hz), 8.53(1H,d,J=2.6 Hz)

Example 1c

Synthesis of 5-nitro-2-(pyrrol-1-yl)benzyl bromide

To a solution in dichloromethane (10 ml) of the compound (239 mg) obtained in Example 1b, triphenyl phosphine (345 mg) and carbon tetrabromide (436 mg) were sequentially added dropwise under cooling with ice. The reaction mixture was stirred for 2 hours under cooling with ice and then concentrated at reduced pressure. The resulting residue was purified by silica gel column chromatography (eluent; ethyl acetate:n-hexane=1:9) to give the titled compound (yield, 47%).

¹H-NMR (CDCl₃) δ:4.47(2H,s), 6.43(2H,t,J=2.0 Hz), 7.00(2H,t,J=2.0 Hz), 7.45(1H,d,J=8.9 Hz), 8.23(1H,,dd,J=2.3,8.9 Hz), 8.46(1H,d,J=2.3 Hz)

Example 1d

Synthesis of N-(5-nitro-2-(pyrrol-1-yl) phenylmethyl)iminodicarboxylic acid di-tert-butyl ester To a mixture of sodium hydride (60% content, 21 mg), iminodicarboxylic acid di-tert-butyl ester (117 mg) and dimethylformamide (5 ml), a solution in dimethylformamide (3 ml) of the compound (137 mg) obtained in Example 1c was added dropwise under cooling with ice. The reaction mixture was stirred for 2 hours at room temperature and then concentrated at reduced pressure. Brine was added to the resulting residue and the mixture was extracted with ethyl acetate. The organic layer was dried with anhydrous sodium sulfate and then concentrated at reduced pressure. The resulting residue was purified by silica gel column chromatography (eluent; ethyl acetate:n-hexane=1:9) to give the titled compound (yield, 74%).

¹H-NMR (CDCl₃) δ:1.47(18H,s), 4.79(2H,s), 6.39(2H,t, J=2.0 Hz), 6.84(2H,t,J=2.0 Hz), 7.42(1H,d,J=8.6 Hz), 8.13 (1H,d,J=2.3 Hz), 8.18(1H,dd,J=2.3,8.6 Hz)

Example 1e

Synthesis of N-(5-amino-2-pyrrol-1-yl) phenylmethyl)iminodicarboxylic acid di-tert-butyl ester A mixture of the compound (120 mg) obtained in Example 1d, 10% palladium-carbon (12 mg) and methanol (30 ml) was stirred at room temperature for 2 hours under a hydrogen atmosphere. The reaction mixture was filtered to remove the palladium-carbon and the resulting filtrate was concentrated at reduced pressure. The resulting residue was purified by silica gel column chromatography (eluent; ethyl acetate:dichloromethane=1:19) to give the titled compound (yield, 63%).

¹H-NMR (CDCl₃) δ:1.43(18H,s), 3.75(2H, brs), 4.55(2H, s), 6.27(2H,t,J=2.0 Hz), 6.48(1H,d,J=2.6 Hz), 6.56(1H,dd, J=2.6,8.2 Hz), 6.70(2H,t,J=2.0 Hz), 7.04(1H,d,J=8.2 Hz)

Example 1f

Synthesis of N-(3-(di-(tert-butoxycarbonyl) aminomethyl)-4-(pyrrol-1-yl)phenyl)thiourea To a mixture of the compound (53 mg) obtained in Example 1e, 4-dimethylaminopyridine (47 mg) and dichloromethane (20 ml), thiophosgene (0.0146 ml) was added dropwise at room temperature. The reaction mixture was stirred at room temperature for 15 minutes and then 28% ammonia solution (10 ml) was added. The reaction mixture was stirred at room temperature for 2 hours and then neutralized with 2 N HCl, followed by extraction with dichloromethane. The organic layer was washed with brine, dried with anhydrous sodium sulfate and then concentrated at reduced pressure. The resulting residue was purified by silica gel column chromatography (eluent; ethyl acetate:n-hexane=3:7) to give the titled compound quantitatively.

¹H-NMR (CDCl₃) δ:1.46(18H,s), 4.67(2H,s), 6.19(2H, brs), 6.34(2H,t,J=2.0 Hz), 6.78(2H,t,J=2.0 Hz), 7.09–7.24 (2H,m), 7.33(1H,d,J=8.3 Hz), 8.04(1H,s)

Example 1g

Synthesis of N-(3-(di-(tert-butoxycarbonyl) aminomethyl)-4-(pyrrol-1-yl)phenyl)-S-ethylisothiourea A mixture of the compound (55 mg) obtained in Example 1f, ethyl iodide (0.039 ml) and acetone (5 ml) was heated under reflux for 14 hours and then concentrated at reduced pressure. Saturated sodium hydrogencarbonate solution was added to the resulting residue and extraction with ethyl acetate was conducted. The organic layer was washed with brine, dried with anhydrous sodium sulfate and then concentrated at reduced pressure. The resulting residue was purified by silica gel column chromatography (eluent; ethyl acetate:n-hexane=4:6) to give the titled compound (yield, 77%).

¹H-NMR (CDCl₃) δ:1.36(3H,t,J=6.9 Hz), 1.43(18H,s), 2.95–3.18(2H,m), 4.40–4.64(2H,m), 4.62(2H,s), 6.30(2H,t, J=2.0 Hz), 6.76(2H,t,J=2.0 Hz), 6.76–6.92(2H,m), 7.19(1H, d,J=8.3 Hz)

Example 1h

Synthesis of N-(3-aminomethyl-4-(pyrrol-1-yl) phenyl)-S-ethylisothiourea dihydrochloride A mixture of the compound (40 mg) obtained in Example 1g and 4 N HCl (10 ml) was stirred at room temperature for 1 hour and then concentrated at reduced pressure to give the titled compound (28 mg; yield, 96%).

¹H-NMR (D₂O) δ:1.44(3H,t,J=7.3 Hz), 3.26(2H,q,J=7.3 Hz), 4.18(2H,s), 6.44–6.54(2H,m), 6.98–7.08(2H,m), 7.54–7.65(3H,m)

Example 2

Synthesis of N-(3-aminomethyl-4-(pyrazol-1-yl) phenyl)-S-ethylisothiourea dihydrochloride

Example 2a

Synthesis of N-(5-nitro-2-(pyrazol-1-yl) phenylmethyl)iminodicarboxylic acid di-tert-butyl ester Sodium hydride (0.54 g) was added to a mixture of pyrazole (1.0 g) and dimethyl sulfoxide (50 ml) under cooling with ice. The reaction mixture was stirred for 1 hour under cooling with ice and then a solution of N-(2-fluoro-5-nitrophenylmethyl)iminodicarboxylic acid di-tert-butyl ester (5.0 g) in dimethyl sulfoxide (50 ml) was added. The reaction mixture was stirred at room temperature for 15 hours and then water was added and extraction with ethyl acetate was conducted. The organic layer was washed with brine, dried with anhydrous sodium sulfate and then concentrated at reduced pressure. The resulting residue was purified by silica gel column chromatography (eluent; ethyl acetate:n-hexane=1:4) to give the titled compound (yield, 73%).

¹H-NMR (CDCl₃) δ:8.22–8.19(2H,m), 7.79–7.78(2H,m), 7.50(1H,d,J=9.6 Hz), 6.53(1H,dd,J=2.3,2.0 Hz), 4.95(2H,s), 1.46(18H,s)

Example 2b

Synthesis of N-(5-amino-2-(pyrazol-1-yl) phenylmethyl)carbamic acid tert-butyl ester Sodium borohydride (2.43 g) was added to a mixture of the compound (4.15 g) obtained in Example 2a, nickel(II) chloride hexahydrate (0.183 g) and methanol (300 ml). The reaction mixture was stirred at room temperature for 55 minutes, then rendered acidic with 2 N HCl, subsequently rendered basic with saturated sodium hydrogencarbonate solution and thereafter concentrated at reduced pressure. Water was added to the resulting residue and extraction with ethyl acetate was conducted. The organic layer was washed with brine, dried with anhydrous sodium sulfate and then concentrated at reduced pressure. The resulting residue was recrystallized from a mixture of ethyl acetate and n-hexane to give the titled compound (yield, 89%).

$^1$H-NMR (CDCl$_3$) δ:7.69(1H,d,J=1.3 Hz), 7.57(1H, d, J=2.0 Hz), 7.06(1H,d,J=8.3 Hz), 6.86–6.83(1H,m), 6.60(1H, dd,J=8.3,2.3 Hz), 6.41(1H,dd,J=2.0,1.3 Hz), 5.62(1H,brs), 4.01(2H,d,J=6.6 Hz), 3.82(2H,brs), 1.43(9H,s)

Example 2c

Synthesis of N-(3-((tert-butoxycarbonyl)aminomethyl)-4-(pyrazol-1-yl)phenyl)thiourea To a mixture of the compound (1.0 g) obtained in Example 2b and acetone (30 ml), benzoyl isothiocyanate (0.52 ml) was added dropwise at room temperature. The reaction mixture was stirred at room temperature for 10 minutes and then concentrated at reduced pressure. Methanol (50 ml) and potassium carbonate (0.53 g) were added to the resulting residue. The reaction mixture was stirred at room temperature for 80 minutes and then concentrated at reduced pressure. Water was added to the resulting residue and extraction with ethyl acetate was conducted. The organic layer was washed with brine, dried with anhydrous sodium sulfate and then concentrated at reduced pressure. The resulting residue was purified by silica gel column chromatography (eluent; ethyl acetate:n-hexane=3:1) to give the titled compound quantitatively.

$^1$H-NMR (CDCl$_3$) δ:8.22(1H,s), 7.76(1H,d,J=1.7 Hz), 7.69(1H,d,J=2.0 Hz), 7.52–7.51(1H,m), 7.35(1H,d,J=8.3 Hz), 7.26–7.24(1H,m), 6.49(1H,dd,J=2.0,1.7 Hz), 6.32(2H, brs), 5.67(1H,t,J=6.3 Hz), 4.18(2H,d,J=6.3 Hz), 1.41(9H,s)

Example 2d

Synthesis of N-(3-((tert-butoxycarbonyl)aminomethyl)-4-(pyrazol-1-yl)phenyl)-S-ethylisothiourea Using the compound obtained in Example 2c as a starting material, the same procedure of Example 1g gave the titled compound (yield, 97%).

$^1$H-NMR (CDCl$_3$) δ:7.71(1H,d,J=1.3 Hz), 7.64(1H,d,J=2.3 Hz), 7.23(1H,d,J=8.3 Hz), 7.13–7.11(1H,m), 6.97–6.83 (1H,m), 6.44(1H,dd,J=2.3,1.3 Hz), 5.67–5.53(1H,m), 4.68–4.50(2H,m), 4.11(2H,d,J=6.3 Hz), 3.15–2.93(2H,m), 1.41–1.35(12H,m)

Example 2e

Synthesis of N-(3-aminomethyl-4-(pyrazol-1-yl)phenyl)-S-ethylisothiourea dihydrochloride Using the compound obtained in Example 2d as a starting material, the same procedure of Example 1h gave the titled compound (yield, 88%).

$^1$H-NMR (DMSO-d$_6$) δ:11.97(1H,,brs), 9.55(2H,brs), 8.61(3H, brs), 8.30(1H,d,J=2.3 Hz), 7.85(1H,d,J=1.3 Hz), 7.82–7.76(1H,,m), 7.67(1H,d,J=8.3 Hz), 7.50(1H,,dd,J=8.3, 2.0 Hz), 6.63(1H,dd,J=2.3,1.3 Hz), 4.06(2H,q,J=4.6 Hz), 3.38(2H,q,J=7.3 Hz), 1.35(3H,t,J=7.3 Hz)

Example 3

Synthesis of N-(3-aminomethyl-4-(1,2,4-triazol-1-yl)phenyl)-S-ethylisothiourea trihydrochloride Substituting 1,2,4-triazole for pyrazole, the same procedure of Example 2 gave the titled compound.

$^1$H-NMR (D$_2$O) δ:8.93(1H,s), 8.77–8.63(2H,m), 8.33 (1H,s), 7.80(1H,d,J=8.3 Hz), 4.19(2H,s), 3.27(2H,q,J=7.3 Hz), 1.44(3H,t,J=7.3 Hz)

Example 4

Synthesis of N-(3-aminomethyl-4-(pyrazol-1-yl)phenyl)-O-ethylisourea dihydrochloride

Example 4a

Synthesis of N-(5-cyanoamino-2-(pyrazol-1-yl)phenylmethyl)carbamic acid tert-butyl ester A mixture of the compound (315 mg) obtained in Example 2c, p-toluenesulfonyl chloride (190 mg) and pyridine (2 ml) was stirred at room temperature for 70 minutes. Water was added to the reaction mixture and extraction with methylene chloride was conducted. The organic layer was washed with brine, dried with anhydrous sodium sulfate and then concentrated at reduced pressure. The resulting residue was purified by silica gel column chromatography (eluent; ethyl acetate:n-hexane=1:1) to give the titled compound (yield, 87%).

$^1$H-NMR (CDCl$_3$) δ:8.06(1H,brs), 7.74(1H,d,J=1.3 Hz), 7.68(1H,d,J=2.3 Hz), 7.28(1H,d,J=8.5 Hz), 7.09(1H,d,J=2.3 Hz), 7.05(1H,dd,J=8.5,2.3 Hz), 6.47(1H,dd,J=2.3,1.3 Hz), 5.77(1H,t,J=6.3 Hz), 4.12(2H,d,J=6.3 Hz), 1.44(9H,s) IR(KBr)2233.16 cm$^{-1}$

Example 4b

Synthesis of N-(3-aminomethyl-4-(pyrazol-1-yl)phenyl)-O-ethylisourea dihydrochloride A mixture of the compound (243 mg) obtained in Example 4a and saturated HCl-ethanol (10 ml) was stirred at room temperature for 29 hours. The reaction mixture was concentrated at reduced pressure and the resulting residue was recrystallized from ethanol-ethyl acetate to give the titled compound (yield, 61%).

$^1$H-NMR (DMSO-d$_6$) δ:11.46(1H,brs), 9.60–9.08(2H,m), 8.54(3H,brs), 8.26(1H,d,J=2.0 Hz), 7.83(1H,d,J=1.6 Hz), 7.68(1H,d,J=2.0 Hz), 7.62(1H,d,J=8.6 Hz), 7.49(1H,,dd,J=8.6,1.6 Hz), 6.60(1H,dd,J=2.0,2.0 Hz), 4.54(2H,q,J=6.9 Hz), 3.99(2H,q,J=4.3 Hz), 1.40(3H,t,J=6.9 Hz)

Example 5

Synthesis of N-(3-aminomethyl-4-(4-methylpyrazol-1-yl)phenyl)-O-ethylisourea dihydrochloride

Example 5a

Synthesis of N-(2-(4-methylpyrazol-1-yl)-5-nitrophenylmethyl)iminodicarboxylic acid di-tert-butyl ester Substituting 4-methylpyrazole for pyrazole, the same procedure of Example 2a gave the titled compound (yield, 3%).

$^1$H-NMR (CDCl$_3$) δ:8.18(1H,d,J=9.6 Hz), 8.17(1H,d,J=2.3 Hz), 7.59(1H,s), 7.53(1H,s), 7.47(1H,dd,J=9.6,2.3 Hz), 4.98(2H,s), 2.18(3H,s), 1.46(18H,s)

Example 5b

Synthesis of N-(5-amino-2-(4-methylpyrazol-1-yl)phenylmethyl)iminodicarboxylic acid di-tert-butyl ester Using the compound obtained in Example 5a as a starting material, the same procedure of Example 2b gave the titled compound (yield, 64%).

¹H-NMR (CDCl₃) δ:7.47(1H,s), 7.31(1H,s), 7.06(1H,d, J=8.3 Hz), 6.58–6.52(2H,m), 4.64(2H,s), 3.72(2H,brs), 2.14 (3H,s), 1.42(18H,s)

Example 5c

Synthesis of N-(3-(di-(tert-butoxycarbonyl) aminomethyl)-4-(4-methylpyrazol-1-yl)phenyl) thiourea Using the compound obtained in Example 5b as a starting material, the same procedure of Example 2c gave the titled compound quantitatively.

¹H-NMR (CDCl₃) δ:7.97(1H,brs), 7.54(1H,s), 7.43(1H, s), 7.35(1H,d,J=7.9 Hz), 7.20–7.14(2H,m), 6.11(2H,brs), 4.81(2H,s), 2.16(3H,s), 1.45(18H,s)

Example 5d

Synthesis of N-(5-cyanoamino-2-(4-methylpyrazol-1-yl)phenylmethyl)carbamic acid tert-butyl ester Using the compound obtained in Example 5c as a starting material, the same procedure of Example 4a gave the titled compound (yield, 75%).

¹H-NMR (CDCl₃) δ:7.52(1H,s), 7.38(1H,s), 7.25(1H,d, J=8.6 Hz), 6.98(1H,dd,J=8.6,2.3 Hz), 6.89(1H,d,J=2.3 Hz), 4.75(2H,s), 2.16(3H,s), 1.42(18H,s) IR(KBr)2235.09 cm⁻¹

Example 5e

Synthesis of N-(3-aminomethyl-4-(4-methylpyrazol-1-yl)phenyl)-O-ethylisourea dihydrochloride Using the compound obtained in Example 5d as a starting material, the same procedure of Example 4b gave the titled compound (yield, 54%).

¹H-NMR (DMSO-d₆) δ:11.44(1H,brs), 9.52–9.05(2H,m), 8.50(3H,brs), 8.02(1H,s), 7.70–7.64(2H,m), 7.57(1H,d,J= 7.9 Hz), 7.52–7.43(1H,m), 4.54(2H,q,J=6.9 Hz), 4.00(2H, q,J=5.3 Hz), 2.14(3H,s), 1.41(3H,t,J=6.9 Hz)

Example 6

Synthesis of N-(3-aminomethyl-4-(4-methylpyrazol-1-yl)phenyl)-S-ethylisothiourea dihydrochloride

Example 6a

Synthesis of N-(3-((tert-butoxycarbonyl) aminomethyl)-4-(4-methylpyrazol-1-yl)phenyl)-S-ethylisothiourea Using the compound obtained in Example 5a as a starting material, the same procedure of Example 1g gave the titled compound (yield, 53%).

¹H-NMR (CDCl₃) δ:7.51(1H,s), 7.40(1H,s), 7.20(1H,d, J=7.9 Hz), 7.13–7.08(1H,m), 6.92–6.78(1H,m), 5.61(1H, brs), 4.68–4.42(2H,m), 4.11(2H,d,J=6.3 Hz), 3.10–2.92(2H, m), 2.15(3H,s), 1.48–1.36(12H,m)

Example 6b

Synthesis of N-(3-aminomethyl-4-(4-methylpyrazol-1-yl)phenyl)-S-ethylisothiourea dihydrochloride Using the compound obtained in Example 6a as a starting material, the same procedure of Example 1h gave the titled compound (yield, 35%).

¹H-NMR (DMSO-d₆) δ:11.88(1H,s), 9.60(2H,s), 8.55 (3H,brs), 8.07(1H,s), 7.78–7.72(1H,m), 7.67(1H,s), 7.62 (1H,d,J=8.6 Hz), 7.50–7.44(1H,m), 4.04(2H,q,J=4.6 Hz), 3.50–3.23(2H,m), 2.15(3H,s), 1.35(3H,t,J=7.3 Hz)

Example 7

Synthesis of N-(3-aminomethyl-2-methyl-4-(pyrazol-1-yl)phenyl)-S-ethylisothiourea dihydrochloride

Example 7a

Synthesis of 4-bromo-5-fluoro-2-nitrotoluene

A mixture of 5-fluoro-2-nitrotoluene (1.00 g), silver nitrate (2.21 g), bromine (0.37 ml) and conc. sulfuric acid (6 ml) was stirred for 1 hour under cooling with ice. The reaction mixture was added dropwise to ice water and then subjected to extraction with chloroform. The organic layer was washed with saturated sodium hydrogencarbonate solution, dried with anhydrous magnesium sulfate and then concentrated at reduced pressure to give the titled compound in admixture with its regioisomer at a ratio of 5:3 (yield, 83%).

¹H-NMR (CDCl₃) δ:2.77(3H,s), 7.39(1H,d,J=11.0 Hz), 8.82(1H,d,J=7.1 Hz)

Example 7b

Synthesis of N-(3-bromo-2-fluoro-6-methyl-5-nitrophenylmethyl)-2,2,2-trifluoroacetamide A mixture of the admixture (1.25 g) obtained in Example 7a, 2,2,2-trifluoroacetamide methanol (0.84 g) and 30% fuming sulfuric acid (5 ml) was stirred at room temperature for 2 hours. The reaction mixture was heated to 70° C., stirred for 1 hour and then cooled to room temperature. The reaction mixture was added dropwise to ice water and then subjected to extraction with chloroform. The organic layer was washed with saturated sodium hydrogencarbonate solution, dried with anhydrous magnesium sulfate and then concentrated at reduced pressure. The residue was recrystallized from hexane-ethyl acetate and the by-product was removed by filtration. The mother liquor was concentrated at reduced pressure to give the titled compound (yield, 45%).

¹H-NMR (CDCl₃) δ:2.56(3H,s), 4.72(2H,dd,J=2.3,5.9 Hz), 6.50–6.75(1H,m), 8.08(1H,d,J=6.6 Hz)

Example 7c

Synthesis of N-(3-bromo-2-fluoro-6-methyl-5-nitrophenylmethyl)carbamic acid tert-butyl ester A mixture of the compound (0.77 g) obtained in Example 7b, conc. HCl (4 ml) and methanol (10 ml) was heated under reflux for 2 hours and then concentrated at reduced pressure. To the resulting residue, 1 N sodium hydroxide solution was added and extraction with chloroform was conducted. The organic layer was dried with anhydrous magnesium sulfate and then concentrated at reduced pressure. To the resulting residue, di-tert-butyl dicarbonate (0.51 g) and dichloromethane (10 ml) were added; the mixture was stirred at room temperature for 2 hours and then concentrated at reduced pressure. The resulting residue was purified by silica gel column chromatography (eluent; ethyl acetate:n-hexane=1:4) to give the titled compound (yield, 83%).

¹H-NMR (CDCl₃) δ:1.33(9H,s), 2.50(3H,s), 4.35–4.50 (2H,m), 5.00–5.15(1H,m), 7.90(1H,d,J=6.3 Hz)

Example 7d

Synthesis of N-(3-bromo-6-methyl-5-nitro-2-(pyrazol-1-yl)phenylmethyl)carbamic acid tert-butyl ester A mixture of the compound (233 mg) obtained in Example 7c, pyrazole (53 mg), sodium carbonate (82 mg)

and dimethylformamide (6 ml) was stirred at 100° C. for 2 hours. Water was added to the reaction mixture and extraction with ethyl acetate was conducted. The organic layer was washed with brine, dried with anhydrous magnesium sulfate and then concentrated at reduced pressure. The resulting residue was purified by silica gel column chromatography (eluent; ethyl acetate:n-hexane=1:3) to give the titled compound (yield, 62%).

$^1$H-NMR (CDCl$_3$) δ:1.43(9H,s), 2.54(3H,s), 2.85–4.80 (2H,m), 5.25–5.45(1H,m), 6.56(1H,dd,J=1.3,2.0 Hz), 7.64 (1H,d,J=2.0 Hz), 7.83(1H,d,J=1.3 Hz), 8.01(1H,s)

Example 7e

Synthesis of N-(3-((tert-butoxycarbonyl) aminomethyl)-2-methyl-4-(pyrazol-1-yl)phenyl) thiourea A mixture of the compound (163 mg) obtained in Example 7d, 10% palladium-carbon (20 mg) and methanol (10 ml) was stirred at room temperature for 6 hours under a hydrogen atmosphere. The reaction mixture was filtered to remove the palladium-carbon and the resulting filtrate was concentrated at reduced pressure. Acetone (10 ml) was added to the resulting residue and benzoyl isothiocyanate (0.064 ml) was then added dropwise at room temperature. The reaction mixture was stirred at room temperature for 16 hours and then water was added, followed by extraction with ethyl acetate. The organic layer was dried with anhydrous magnesium sulfate and then concentrated at reduced pressure. The resulting residue was purified by silica gel column chromatography (eluent; ethyl acetate:n-hexane=1:3) to give N-benzoyl-N'-(3-((tert-butoxycarbonyl)aminomethyl)-2-methyl-4-(pyrazol-1-yl)phenyl)thiourea (yield, 78%). A mixture of the resulting thiourea compound (143 mg), potassium carbonate (64 mg) and methanol (4 ml) was stirred at room temperature for 2 hours. The reaction mixture was concentrated at reduced pressure and water was added to the resulting residue, followed by extraction with ethyl acetate. The organic layer was washed with brine, dried with anhydrous magnesium sulfate and then concentrated at reduced pressure. The resulting residue was purified by silica gel column chromatography (eluent; ethyl acetate:n-hexane=1:2) to give the titled compound quantitatively.

$^1$H-NMR (CDCl$_3$) δ:1.43(9H,s), 2.43(3H,s), 4.10(2H,d, J=5.9 Hz), 5.70–5.80(1H,m), 6.00–6.45(2H,m), 6.49(1H,dd, J=2.0,2.3 Hz), 7.19(1H,d,J=8.3 Hz), 7.29(1H,d,J=8.3 Hz), 7.67(1H,,d,J=2.3 Hz), 7.76(1H,d,J=2.0 Hz), 8.67(1H,s)

Example 7f

Synthesis of N-(3-((tert-butoxycarbonyl) aminomethyl)-2-methyl-4-(pyrazol-1-yl)phenyl)-S-ethylisothiourea A mixture of the compound (47 mg) obtained in Example 7e, ethyl iodide (0.026 ml) and acetonitrile (1 ml) was heated under reflux for 4 hours and then concentrated at reduced pressure. Saturated sodium hydrogencarbonate solution was added to the resulting residue and extraction with chloroform was conducted. The organic layer was dried with anhydrous magnesium sulfate and then concentrated at reduced pressure. The resulting residue was purified by silica gel column chromatography (eluent; chloroform:methanol=15:1) to give the titled compound (yield, 95%).

$^1$H-NMR (CDCl$_3$) δ:1.39(3H,t,J=7.3 Hz), 1.44(9H,s), 2.31(3H,s), 3.10(2H,q,J=7.3 Hz), 4.07(2H,d,J=5.9 Hz), 4.20–5.00(2H,m), 5.55–5.70(1H,m), 6.44(1H,,dd,J=2.0,2.3 Hz), 6.88(1H,d,J=8.3 Hz), 7.08(1H,d,J=8.3 Hz), 7.62(1H,, d,J=2.3 Hz), 7.72(1H,d,J=2.0 Hz)

Example 7g

Synthesis of N-(3-aminomethyl-2-methyl-4-(pyrazol-1-yl)phenyl)-S-ethylisothiourea dihydrochloride A mixture of the compound (47 mg) obtained in Example 7f and 6 N HCl (6 ml) was stirred at room temperature for 3 hours. The reaction mixture was concentrated at reduced pressure to give the titled compound (yield, 93%).

$^1$H-NMR (DMSO-d$_6$) δ:1.35(3H,t,J=7.3 Hz), 2.39(3H,s), 3.20–3.45(2H,m), 3.80–4.05(2H,m), 6.63(1H,dd,J=2.0,2.3 Hz), 7.50(2H,s), 7.86(1H,d,J=2.0 Hz), 8.26(1H,d,J=2.3 Hz), 8.40–8.65(3H,m), 8.65–10.00(2H,m), 11.9(1H,s)

MS(m/z)289(M$^+$)

C$_{14}$H$_{21}$N$_5$SCl$_2$:

Calcd: C, 46.41; H, 5.84; N, 19.33

Found: C, 46.34; H, 6.09; N, 19.05

Example 8

Synthesis of N-(3-aminomethyl-2-methyl-4-(pyrazol-1-yl)phenyl)-O-ethylisourea dihydrochloride Example 8a Synthesis of N-(3-cyanoamino-2-methyl-6-(pyrazol-1-yl)phenylmethyl)carbamic acid tert-butyl ester Using the compound obtained in Example 7e as a starting material, the same procedure of Example 4a gave the titled compound (yield, 88%).

$^1$H-NMR (CDCl$_3$) δ:1.44(9H,s), 2.35(3H,s), 4.06(2H,d, J=5.9 Hz), 5.70–5.87(1H,m), 6.46(1H,dd,J=1.6,2.6 Hz), 6.90(1H,s), 7.18(1H,d,J=8.6 Hz), 7.25(1H,d,J=8.6 Hz), 7.62 (1H,d,J=2.6 Hz), 7.74(1H,d,J=1.6 Hz)

Example 8b

Synthesis of N-(3-aminomethyl-2-methyl-4-(pyrazol-1-yl)phenyl)-O-ethylisourea dihydrochloride Using the compound obtained in Example 8a as a starting material, the same procedure of Example 4b gave the titled compound (yield, 40%).

$^1$H-NMR (DMSO-d$_6$) δ:1.37(3H,t,J=7.3 Hz), 2.43(3H,s), 3.90–3.98(2H,m), 4.50(2H,q,J=7.3 Hz), 6.62(1H,dd,J=2.0, 2.3 Hz), 7.46(1H,d,J=8.9 Hz), 7.53(1H,d,J=8.9 Hz), 7.85 (1H,d,J=2.0 Hz), 8.23(1H,d,J=2.3 Hz), 8.33–8.53(3H,m), 8.60–9.60(2H,m), 11.10(1H,s)

Test Examples

Test Example 1

The ability of selected compounds of the present invention to inhibit the presently known three NOS isoforms was evaluated in comparison with five existing NOS inhibitors.

The control compounds were as follows:

L-NA,
L-CPA,
L-MIN,

L-EIN,
L-NAME.

Crude enzymes of the respective NOS isoforms were prepared by the following procedures (Nagafuji et al., Neuroreport 6, 1541–1545, 1995).

The crude enzyme of nNOS was prepared by the following procedure. Normal untreated male Sprague Dawley (SD) rats (body weight, 300–400 g) were decapitated; the whole brain was immediately taken out from each animal and the cerebral cortex was separated on ice. Then, 5 volumes of 50 mM Tris-HCl containing 1 mM DTT (pH 7.4) was added and the mixture was homogenized for 3 min and centrifuged at 1,000×g for 10 min. The resulting supernatant was further centrifuged at 100,000×g for 60 min and a soluble cytosolic fraction of the finally obtained supernatant was used as the crude enzyme of nNOS.

The crude enzyme of eNOS was prepared by the following procedure. Cow pulmonary arterial endothelium cells (CPAE) were cultured in a MEM medium containing 20% FBS. Several days later, the cells were detached from the flask using a 0.25% trypsin solution containing 1 mM EDTA and, after addition of a suitable amount of FBS, centrifuged at 1,000 rpm for 10 min. A suitable amount of Ca- and Mg-free phosphate buffer (pH 7.4) was added to the precipitating cells and they were centrifuged at 1,000 rpm for 10 min. The same step was repeated to wash the cells which, upon addition of 50 mM Tris-HCl (pH 7.4) containing 1% Triton X-100 and 1 mM DTT, were left to stand in ice for 1 h. Subsequently, the mixture was homogenized for 3 min and kept in ice for 30 min with occasional stirring. Finally, the mixture was centrifuged at 100,000×g for 60 min and the resulting supernatant was used as the crude enzyme of eNOS.

The method of measuring NOS activity was basically the same as already reported by the present inventors and consisted of determining quantitatively the conversion of a substrate L-[$^3$H]arginine to a reaction product L-[$^3$H] citrulline (Nagafuji et al., in Brain Edema IX (Ito et al, eds.) 60, pp. 285–288, 1994; Nagafuji et al., Neuroreport 6, 1541–1545, 1995)

The reaction solution consisted of 100 nM L-[$^3$H] arginine, a prepared crude NOS enzyme sample (10–30 μg/ml protein), 1.25 mM CaCl$_2$, 1 mM EDTA, 10 μg/ml calmodulin, 1 mM NADPH, 100 μM tetrahydrobiopterine, 10 μM FAD, 10 μM FMN and 50 mM Tris-HCl (pH 7.4), to which one of the compounds of the invention or one of the control compounds was added.

The reaction was started by addition of L-[$^3$H] arginine. After incubation at 37° C. for 10 min, the reaction was terminated by addition of 2 ml of 50 mM Tris-HCl (pH 5.5) containing 1 mM EDTA and placing the mixture on ice. The reaction solution was passed through a cation-exchange resin column (Dowex AG50WX-8, Na$^+$ form, 3.2 ml) to separate the reaction product L-[$^3$H] citrulline from the unreacted residual substrate L-[$^3$H] arginine. The eluate was combined with another eluate resulting from the passage of a given amount of distilled water through the column and put into a minivial for recovery of L-[$^3$H] citrulline. Thereafter, a scintillation fluid was added and the contained radioactivity was measured with a liquid scintillation counter to determine the amount of L-[$^3$H] citrulline.

The activity of nNOS or eNOS was determined by subtracting the activity detected in the absence of CaCl$_2$ and calmodulin from the activity detected in the presence of CaCl$_2$ and calmodulin. The protein concentration of each crude enzyme sample was determined with a micro-assay kit of Bio Rad Co. Each experiment was conducted in a duplicate.

Table 2 lists the values of IC$_{50}$ (the concentration necessary to inhibit 50% activity) of all test compounds against each NOS isoform. The table also lists the ratios of IC$_{50}$ values to each other as an index of selectivity.

TABLE 2

| Example No. or Control Compound | IC$_{50}$ (nM) | | | Ratio of IC$_{50}$ | | |
|---|---|---|---|---|---|---|
| | nNOS (type 1) | eNOS (type 3) | iNOS (type 2) | eNOS/ nNOS | iNOS/ nNOS | eNOS/ inos |
| 1 | 3.7 | 1920 | 7930 | 515 | 2120 | 0.243 |
| L-MIN | 5.7 | 35.8 | 248 | 6.28 | 43.3 | 0.145 |
| 2 | 6.3 | 5130 | 20500 | 816 | 3260 | 0.250 |
| L-EIN | 8.4 | 732 | 6760 | 87.2 | 805 | 0.108 |
| L-NA | 16.9 | 68.2 | 3460 | 4.03 | 205 | 0.0197 |
| 7 | 22.4 | 21100 | n. d. | 943 | — | — |
| L-CPA | 27.3 | 1540 | 7150 | 56.4 | 262 | 0.215 |
| L-NAME | 79.4 | 670 | 13500 | 8.44 | 171 | 0.0495 |

Notes: Symbol "n.d." means "not determined", and "—" means "uncalculable".

Table 2 demonstrates the following two points:
1. The compound of Example 1 has more potent nNOS inhibiting activity than L-MIN which was the most potent of the existing NOS inhibitors under test;
2. The compounds of Examples 1, 2 and 7 have higher selectivity for nNOS inhibition over eNOS than L-EIN which was the best of the existing NOS inhibitors under test in terms of selective inhibition of nNOS.

Industrial Applicability

The compounds of the present invention exhibit an outstanding nNOS inhibiting activity or more selective inbihition of nNOS over enos and are useful as therapeutics of cerebrovascular diseases [cerebral hemorrhage, subarachnoid hemorrhage, cerebral infarction (atherothrombotic infarction, lacunar infarction and cardiogenic embolism), transient ischemic attack and cerebral edema], traumatic brain injury, spinal injury, pains [headache (migraine, tension headache, cluster headache and chronic paroxysmal headache)], Parkinson's disease, Alzheimer's disease, seizure, and morphine tolerance or dependence.

What is claimed is:

1. A compound represented by the formula (1), or a tautomer, stereoisomer or optically active form of the compound or a pharmaceutically acceptable salt thereof:

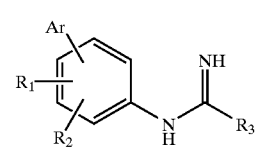

(1)

wherein

R$_1$ is an optionally substituted aminoalkyl group having 1–6 carbon atoms in the alkyl moiety;

R$_2$ is a hydrogen atom, a lower alkyl group or a halogen atom;

R$_3$ is an optionally substituted lower alkyl group, SR$_4$, OR$_4$ or NR$_5$R$_6$ provided that R$_4$ is a lower alkyl group that may be substituted by a halogen atom and R$_5$ and R$_6$, which may be the same or different, represent a hydrogen atom, a lower alkyl group or a nitro group or, when taken together, may form a 3- to 6-membered ring; and Ar is an optionally substituted 5-membered aromatic heterocyclic group selected from the group consisting of pyrrolyl, pyrazolyl and triazolyl.

2. The compound of the formula (1) according to claim 1, or a tautomer, stereoisomer or optically active form of the compound or a pharmaceutically acceptable salt thereof, in which $R_3$ is $OR_4$.

3. The compound of the formula (1) according to claim 1, or a tautomer, stereoisomer or optically active form of the compound or a pharmaceutically acceptable salt thereof, in which:
   $R_3$ is an optionally substituted lower alkyl group, $SR_4$, or $NR_5R_6$; and
   Ar is a substituted 5-membered aromatic heterocyclic group selected from the group consisting of pyrrolyl, pyrazolyl and triazolyl.

4. The compound of the formula (1) according to claim 1, or a tautomer, stereoisomer or optically active form of the compound or a pharmaceutically acceptable salt thereof, in which;
   $R_3$ is an optionally substituted lower alkyl group, $SR_4$, or $NR_5R_6$; and
   Ar is a 5-membered aromatic heterocyclic group selected from the group consisting of pyrrolyl, pyrazolyl and triazolyl.

5. The compound of the formula (1) according to claim 1, or a tautomer, stereoisomer or optically active form of the compound or a pharmaceutically acceptable salt thereof, in which $R_1$ is an aminomethyl group.

6. The compound of the formula (1) according to claim 1, or a tautomer, stereoisomer or optically active form of the compound or a pharmaceutically acceptable salt thereof, in which Ar is a pyrrol-1-yl group or a pyrazol-1-yl group.

7. The compound of the formula (1) according to claim 1, or a tautomer, stereoisomer or optically active form of the compound or a pharmaceutically acceptable salt thereof, in which except for $R_2$ and Ar, the benzene nucleus is m-substituted.

8. The compound according to claim 1 or a tautomer, stereoisomer or optically active form of the compound or a pharmaceutically acceptable salt thereof, said compound being selected from the group consisting of:

N-(3-aminomethyl-4-(pyrazol-1-yl)phenyl)-S-ethyl isothiourea;
N-(3-aminomethyl-4-(pyrrol-1-yl)phenyl)-S-ethyl isothiourea; and
N-(3-aminomethyl-2-methyl-4-(pyrazol-1-yl)phenyl)-S-ethylisothiourea.

9. A pharmaceutical composition containing the compound according to claim 1 as an active ingredient and a pharmaceutically acceptable carrier.

10. A method for the treatment of cerebrovascular disease, comprising administering to a patient in need thereof an amount sufficient for said therapy of a compound according to claim 1.

11. The method of claim 10, wherein said patient is a patient in need of treatment for cerebral hemorrhage.

12. The method of claim 10, wherein said patient is a patient in need of treatment for subarachnoid hemorrhage.

13. The method of claim 10, wherein said patient is a patient in need of treatment for cerebral infarction.

14. The method of claim 13, wherein said patient is a patient in need of treatment for atherothrombotic infarction.

15. The method of claim 13, wherein said patient is a patient in need of treatment for lacunar infarction.

16. The method of claim 13, wherein said patient is a patient in need of treatment for cardiogenic embolism.

17. The method of claim 10, wherein said patient is a patient in need of treatment for transient ischemic attack (TIA).

18. The method of claim 10, wherein said patient is a patient in need of treatment for cerebral edema.

19. A method for treatment of traumatic brain injury, comprising administering to a patient in need thereof an amount sufficient for said therapy of a compound according to claim 1.

20. A method for the treatment of spinal injury, comprising administering to a patient in need thereof an amount sufficient for said therapy of a compound according to claim 1.

21. A method for the treatment of pain, comprising administering to a patient in need thereof an amount sufficient for said therapy of an analegesic compound according to claim 1.

22. The method according to claim 21, wherein said patient is a person suffering from headache.

23. The method according to claim 22, wherein said patient is a person suffering from migraine headache.

24. The method according to claim 22, wherein said patient is a person suffering from tension headache.

25. The method according to claim 22, wherein said patient is a person suffering from cluster headache or chronic paroxysmal headache.

26. A method for the treatment of Parkinson's disease, comprising administering to a patient in need thereof an amount effective for said therapy of a compound according to claim 1.

27. A method for the treatment of Alzheimer's disease, comprising administering to a patient in need thereof an amount effective for said therapy of a compound according to claim 1.

28. A method for the treatment of seizure, comprising administering to a patient in need thereof an amount effective for said therapy of a compound according to claim 1.

* * * * *